(12) United States Patent
Alig et al.

(10) Patent No.: US 6,518,296 B1
(45) Date of Patent: Feb. 11, 2003

(54) SUBSTITUTED 3-THIOCARBAMOYLPYRAZOLES

(75) Inventors: Bernd Alig, Königswinter (DE); Albrecht Marhold, Leverkusen (DE); Jörn Stölting, Köln (DE); Wolfgang Gau, Wuppertal (DE); Christoph Erdelen, Leichlingen (DE); Andreas Turberg, Haan (DE); Norbert Mencke, Leverkusen (DE); Olaf Hansen, Langenfeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/701,364

(22) Filed: Nov. 28, 2000

(30) Foreign Application Priority Data

Jun. 2, 1998 (DE) .......................... 198 24 487

(51) Int. Cl.⁷ .................... A01N 43/56; C07D 231/44; C07D 231/18
(52) U.S. Cl. .................. 514/407; 514/406; 548/366.1; 548/366.7; 548/367.4; 548/368.4; 548/369.1; 548/369.7
(58) Field of Search ............... 548/366.1, 366.7, 548/367.4, 368.4, 369.1, 369.7; 514/406, 407

(56) References Cited

U.S. PATENT DOCUMENTS

| | | | |
|---|---|---|---|
| 4,945,165 A | 7/1990 | Jensen-Korte et al. | 201/362 |
| 5,232,940 A | 8/1993 | Hatton et al. | 295/407 |
| 5,547,974 A | 8/1996 | Hatton et al. | 295/406 |
| 5,580,843 A | 12/1996 | Stetter et al. | 659/341 |
| 5,608,077 A | 3/1997 | Hatton et al. | 295/365.1 |
| 5,629,335 A | 5/1997 | Manning et al. | 514/407 |
| 5,631,381 A | 5/1997 | Huang et al. | 548/367.4 |
| 5,688,966 A | 11/1997 | Bobrow | 458/455 |
| 5,714,191 A | 2/1998 | Hatton et al. | 295/532 |
| 5,753,030 A | 5/1998 | Flatt et al. | 807/495 |
| 5,883,112 A | 3/1999 | Pilato et al. | 514/404 |
| 5,916,618 A | 6/1999 | Hatton et al. | 295/532 |
| 6,015,910 A | 1/2000 | Wu | 548/367.7 |
| 6,037,312 A | 3/2000 | Takashima et al. | 504/271 |

FOREIGN PATENT DOCUMENTS

| | | |
|---|---|---|
| EP | 0 418 016 | 5/1995 |
| EP | 0 738 713 | 2/2000 |
| WO | 93/06089 | 4/1993 |
| WO | 98/24769 | 6/1998 |
| WO | 98/28279 | 7/1998 |

*Primary Examiner*—Patricia L. Morris
(74) *Attorney, Agent, or Firm*—Richard E. L. Henderson; John E. Mrozinski

(57) ABSTRACT

The invention relates to novel substituted 3-thiocarbamoylpyrazoles of general formula (I), wherein m, n, $R^1$, $R^2$, $R^3$ and Ar have the meanings cited in the description. The invention further relates to methods for the production and use thereof as pesticides.

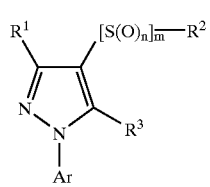

(I)

8 Claims, No Drawings

SUBSTITUTED 3-THIOCARBAMOYLPYRAZOLES

The invention relates to novel substituted 3-thiocarbamoylpyrazoles, to a plurality of processes for their preparation and to their use as pesticides.

It is already known that various substituted amino pyrazoles are highly effective against pests (cf., for example, WO 97/22 593, WO 97/44 340, EP 295 117, EP 807 668, EP 738 713, EP 352 944, EP 201 852, EP 418 016, EP 659 745, U.S. Pat. No. 5,688,966, U.S. Pat. No. 5 631 381, U.S. Pat. No. 5 629 335). However, in particular in the case of certain pests and/or at low application concentrations, the efficacy and/or persistency of the prior-art compounds is not entirely satisfactory in all areas of use.

This invention, accordingly, provides novel substituted 3-thiocarbamoylpyrazoles of the general formula (I):

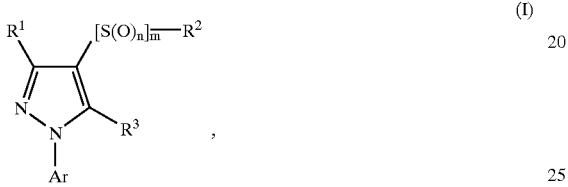

in which
$R^1$ represents $H_2N$—CS—,
m represents the number 0 or 1,
n represents the number 0, 1 or 2,
$R^2$ represents alkyl, alkenyl, alkinyl, cyanoalkyl, thiocyanatoalkyl, nitroalkyl, alkylthioalkyl, alkylsulphinylalkyl, alkylsulphonylalkyl, halogenoalkylthioalkyl, halogenoalkylsulphinylalkyl, halogenoalkylsulphonylalkyl, alkenylthioalkyl, alkenylsulphinylalkyl, alkenylsulphonylalkyl, alkinylthioalkyl, alkinylsulphinylalkyl, alkinylsulphonylalkyl, alkoxycarbonylalkyl, halogenoalkoxycarbonylalkyl, alkoxycarbonyl, alkenyloxycarbonyl, halogenoalkoxycarbonyl, alkylcarbonyl, alkoxyalkyl, halogenoalkoxyalkyl, alkoxyalkylthioalkyl, alkoxyalkylsulphinylalkyl, alkoxyalkylsulphonylalkyl, halogenoalkoxyalkylthioalkyl, halogenoalkoxyalkylsulphinylalkyl, halogenoalkoxyalkylsulphonylalkyl, alkylaminoalkyl, dialkylaminoalkyl, trialkylsilylalkyl; in each case optionally substituted cycloalkyl, cycloalkenyl or cycloalkylalkyl; and also represents aryl, heteroaryl, arylalkyl, heteroarylalkyl, aryloxyalkyl, arylthioalkyl, arylsulphinylalkyl, arylsulphonylalkyl, arylalkyloxyalkyl, arylalkylthioalkyl, arylalkylsulphinylalkyl or arylalkylsulphonylalkyl, each of which is optionally substituted in the aryl moiety or heteroaryl moiety,
$R^2$ for the meaning of m=0 additionally represents thiocyanato, halogen, nitro, cyano, hydroxyl, halogenoalkyl, halogenoalkenyl, chlorosulphonyl, alkoxy, halogenoalkoxy, alkenyloxy, halogenoalkenyloxy, alkylcarbonyloxy, formyl, trialkylsilylethinyl, optionally substituted aryloxy or represents one of the following groupings:
—$NHR^4$, —$NR^4R^5$, —$NHNH_2$, —$CONH_2$, —$CSNH_2$, —$CONR^4R^5$, —$SO_2NR^4R^5$, —$CR^6$=$NOR^7$, —$CH(OH)R^8$ or —$CH(CN)OR^9$,
where $R^4$ and $R^5$ independently of one another represent hydrogen, cyano, alkyl or in each case optionally substituted aryl or aralkyl,
$R^6$ represents hydrogen or alkyl,
$R^7$ represents hydrogen, alkyl or optionally substituted aralkyl,
$R^8$ represents alkyl or halogenoalkyl and
$R^9$ represents alkyl,
$R^3$ represents hydrogen, amino, halogen or represents one of the following groupings:
—NH—CO—$R^{10}$, —$NHR^{11}$, —$OR^{12}$, —$SR^{12}$ or —$NR^{13}$—CX—C($R^{14}$, $R^{15}$, $R^{16}$)
where
$R^{10}$ represents alkyl, halogenoalkyl, alkoxyalkyl or in each case optionally substituted phenyl, phenoxy or pyridyl,
$R^{11}$ represents alkyl, alkenyl, alkinyl, formyl, alkylcarbonyl, halogeno-alkylcarbonyl or alkoxycarbonyl,
$R^{12}$ represents alkyl, alkenyl, alkinyl, optionally substituted aralkyl, dialkylaminoalkyl or represents the grouping —P(=Y)($OR^{17}$)($SR^{18}$),
where
$R^{17}$ and $R^{18}$ independently of one another represent alkyl and
Y represents oxygen or sulphur,
$R^{13}$ represents hydrogen, alkyl, alkoxyalkyl, propargyl, allyl, alkoxycarbonyl, alkylcarbonyl, optionally substituted benzyl or the grouping —CO—C($R^{14}$, $R^{15}$, $R^{16}$),
$R^{14}$ represents hydrogen, alkyl, halogenoalkyl, halogen or optionally substituted phenyl and
$R^{15}$ represents hydrogen, alkyl, halogenoalkyl, halogen, halalkoxyalkyl, alkylthioalkyl, alkylsulphinylalkyl, alkylsulphonylalkyl, alkoxy(alkoxy)$_r$alkyl where r=0 to 4, hydroxyl, alkoxycarbonylalkyl or alkoxy, or
$R^{14}$ and $R^{15}$ together with the carbon atom to which they are attached represent a 3- to 7-membered ring system having optionally up to two heteroatoms and
$R^{16}$ represents hydroxyl, alkoxy, halalkoxy, alkoxy(alkoxy)$_p$ where p=1 to 4 or halalkoxy(alkoxy)$_q$ where q=1 to 4, and
X represents oxygen or sulphur, and
Ar represents in each case optionally substituted phenyl or pyridyl.

Furthermore, it has been found that the novel substituted 3-thiocarbamoylpyrazoles of the formula (I) are obtained when a) 3-cyanopyrazole derivatives of the formula (II):

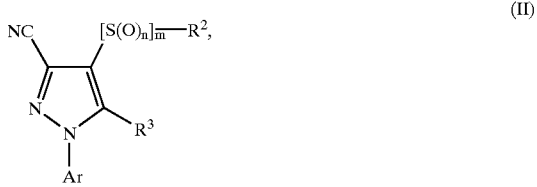

in which
Ar, $R^2$, $R^3$, m and n are as defined above,
are reacted with hydrogen sulphide, if appropriate in the presence of a reaction auxiliary and if appropriate in the presence of a diluent;

or when b) 3-thiocarbamoylpyrazole derivatives of the formula (III)

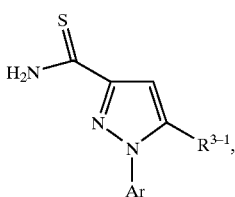

in which
Ar is as defined above and
$R^{3-1}$ represents one of the groupings below:

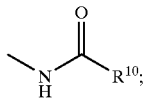

—$NHR^{11}$, —$OR^{12}$ or —$NR^{13}$—CX—C($R^{14}$, $R^{15}$, $R^{16}$),
where
$R^{10}$ to $R^{16}$ and X are as defined above,
are reacted with sulphenyl halides of formula (IV):

$$Hal—S—R^2 \qquad (IV)$$

in which
$R^2$ is as defined above and
Hal represents halogen, in particular chlorine or bromine,
if appropriate in the presence of a diluent and if appropriate in the presence of a reaction auxiliary;
or when
c) the 3-thiocarbamoylpyrazole derivatives, obtainable according to process (a) or (b), of the formula (Ia):

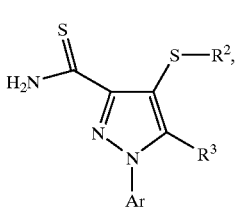

in which
Ar, $R^2$ and $R^3$ are as defined above,
are oxidized with oxidizing agents, if appropriate in the presence of a diluent and if appropriate in the presence of a catalyst.

Finally, it has been found that the novel 3-thiocarbamoylpyrazole derivatives of the formula (I) have highly pronounced biological properties and are suitable especially for controlling animal pests, in particular insects, arachnids and nematodes, encountered in agriculture, in forests, in the protection of stored products and in the protection of materials and in the hygiene sector.

The formula (I) provides a general definition of the compounds according to the invention.

Preferred substituents or ranges of the radicals listed in the formulae mentioned above and below are illustrated below.

$R^2$ preferably represents $(C_1-C_6)$-alkyl, $(C_2-C_6)$-alkenyl, $(C_2-C_6)$-alkinyl, cyano-$(C_1-C_4)$-alkyl, thiocyanato-$(C_1-C_4)$-alkyl, nitro-$(C_1-C_4)$-alkyl, $(C_1-C_6)$-alkylthio-$(C_1-C_4)$-alkyl, $(C_1-C_6)$-alkylsulphinyl-$(C_1-C_4)$-alkyl, $(C_1-C_6)$-alkyl-sulphonyl-$(C_1-C_4)$-alkyl, $(C_1-C_4)$-halogenoalkylthio-$(C_1-C_4)$-alkyl having 1 to 6 halogen atoms, $(C_1-C_4)$-halogenoalkylsulphinyl-$(C_1-C_4)$-alkyl having 1 to 6 halogen atoms, $(C_1-C_4)$-halogenoalkylsulphonyl-$(C_1-C_4)$-alkyl having 1 to 6 halogen atoms, $(C_2-C_6)$-alkenylthio-$(C_1-C_4)$-alkyl, $(C_2-C_6)$-alkenylsulphinyl-$(C_1-C_4)$-alkyl, $(C_2-C_6)$-alkenylsulphonyl-$(C_1-C_4)$-alkyl, $(C_2-C_6)$-alkinylthio-$(C_1-C_4)$-alkyl, $(C_2-C_6)$-alkinylsulphinyl-$(C_1-C_4)$-alkyl, $(C_2-C_6)$-alkinylsulphonyl-$(C_1-C_4)$-alkyl, $(C_1-C_4)$-alkoxy-carbonyl-$(C_1-C_4)$-alkyl, $(C_1-C_4)$-halogenoalkoxy-carbonyl-$(C_1-C_4)$-alkyl having 1 to 5 halogen atoms, $(C_1-C_6)$-alkoxy-carbonyl, $(C_1-C_6)$-alkyl-carbonyl, $(C_1-C_6)$-alkoxy-$(C_1-C_4)$-alkyl, $(C_1-C_6)$-halogenoalkoxy-$(C_1-C_4)$-alkyl having 1 to 6 halogen atoms, $(C_1-C_4)$-alkoxy-$(C_1-C_4)$-alkylthio-$(C_1-C_4)$-alkyl, $(C_1-C_4)$-alkoxy-$(C_1-C_4)$-alkylsulphinyl-$(C_1-C_4)$-alkyl, alkoxy-$(C_1-C_4)$-alkylsulphonyl-$(C_1-C_4)$-alkyl, $(C_1-C_4)$-halogenoalkoxy-$(C_1-C_4)$-alkylthio-$(C_1-C_4)$-alkyl having 1 to 5 halogen atoms, $(C_1-C_4)$-halogenoalkoxy-$(C_1-C_4)$-alkylsulphinyl-$(C_1-C_4)$-alkyl having 1 to 5 halogen atoms, $(C_1-C_4)$-halogenoalkoxy-$(C_1-C_4)$-alkylsulphonyl-$(C_1-C_4)$-alkyl having 1 to 5 halogen atoms, $(C_1-C_4)$-alkylamino-$(C_1-C_4)$-alkyl, di-$(C_1-C_4)$-alkylamino-$(C_1-C_4)$-alkyl, tri-$(C_1-C_4)$-alkylsilyl-$(C_1-C_4)$-alkyl;

represents $(C_3-C_6)$-cycloalkyl, $(C_5-C_6)$-cycloalkenyl or $(C_3-C_6)$-cycloalkyl-$(C_1-C_2)$-alkyl, each of which is optionally mono- to pentasubstituted by identical or different substituents, possible substituents being: $(C_1-C_4)$-alkyl, $(C_1-C_4)$-alkoxy, halogen, $(C_1-C_4)$-halogenoalkyl having 1 to 5 halogen atoms and $(C_1-C_4)$-halogenoalkoxy having 1 to 5 halogen atoms;
and represents phenyl, phenyl-$(C_1-C_2)$-alkyl, phenoxy-$(C_1-C_2)$-alkyl, phenylthio-$(C_1-C_2)$-alkyl, phenylsulphinyl-$(C_1-C_2)$-alkyl, phenylsulphonyl-$(C_1-C_2)$-alkyl, phenyl-$(C_1-C_2)$-alkyloxy-$(C_{1-2})$-alkyl, phenyl-$(C_1-C_2)$-alkylthio-$(C_1-C_2)$-alkyl, phenyl-$(C_1-C_2)$-alkylsulphinyl-$(C_1-C_2)$-alkyl, phenyl-$(C_1-C_2)$-alkylsulphonyl-$(C_1-C_2)$-alkyl, pyridyl or pyridyl-$(C_1-C_2)$-alkyl, each of which is optionally mono- to trisubstituted by identical or different substituents, possible phenyl or pyridyl substituents being: halogen, $(C_1-C_6)$-alkyl, $(C_2-C_6)$-alkenyl, $(C_{1-6})$-alkoxy, $(C_2-C_6)$-alkenyloxy, $(C_1-C_4)$-alkylthio, $(C_1-C_4)$-alkylsulphinyl, $(C_1-C_4)$-alkyl-sulphonyl; $(C_1-C_6)$-halogenoalkyl, $(C_2-C_4)$-halogenoalkenyl, $(C_{1-4})$-halogenoalkoxy, $(C_1-C_4)$-halogenoalkylthio, $(C_1-C_4)$-halogenoalkylsulphinyl and $(C_1-C_4)$-halogenoalkylsulphonyl having in each case 1 to 5 halogen atoms; cyano, nitro, hydroxyl, hydrazino, $(C_1-C_6)$-dialkylhydrazino, amino, $(C_1-C_6)$-alkylamino, di-$(C_1-C_6)$-alkylamino, $(C_1-C_6)$-alkylimino, $(C_1-C_4)$-alkyl-carbonyl, $(C_1-C_4)$-alkyl-carbonyloxy, phenyl or phenoxy, each of which is optionally mono- to trisubstituted by identical or different substituents from the group consisting of halogen, $(C_1-C_4)$-alkyl, $(C_1-C_4)$-halogenoalkyl having 1 to 5 halogen atoms, $(C_1-C_4)$-alkoxy and $(C_1-C_4)$-halogenoalkoxy and $(C_1-C_4)$-halogenoalkylthio having in each case 1 to 5 halogen atoms, $SF_5$ or the grouping

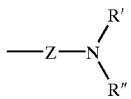

where
R' and R" independently of one another represent hydrogen or $(C_1-C_6)$-alkyl and
Z represents —CO or —$SO_2$.

$R^2$ for the meaning of m=0 additionally preferably represents thiocyanato, chlorine, bromine, iodine, nitro, cyano, hydroxyl, chlorosulphonyl, $(C_1-C_4)$-alkoxy, $(C_2-C_4)$-alkenyloxy; $(C_1-C_4)$-halogenoalkyl, $(C_2-C_4)$-halogeno-alkenyl, $(C_1-C_4)$-halogenoalkoxy and $(C_2-C_4)$-halogenoalkenyloxy having in each case 1 to 5 halogen atoms; $(C_1-C_4)$-alkyl-carbonyloxy, formyl, tri-$(C_1-C_4)$-alkylsilylethinyl; represents phenoxy which is optionally mono- to pentasubstituted by identical or different substituents, possible substituents being the phenyl substituents already mentioned above for $R^2$, or preferably represents one of the following groupings:

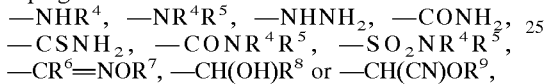

where
$R^4$ and $R^5$ independently of one another preferably represent hydrogen, cyano, $(C_1-C_4)$-alkyl or represent phenyl or benzyl, each of which is optionally mono- to pentasubstituted by identical or different substituents, possible substituents being the phenyl substituents already mentioned above for $R^2$.

$R^6$ preferably represents hydrogen or $(C_1-C_4)$-alkyl.

$R^7$ preferably represents hydrogen, $(C_1-C_4)$-alkyl or benzyl, which is optionally mono- to pentasubstituted by identical or different substituents, possible substituents being the phenyl substituents already mentioned above for $R^2$.

$R^8$ preferably represents $(C_1-C_4)$-alkyl or $(C_1-C_4)$-halogenoalkyl having 1 to 5 halogen atoms.

$R^9$ preferably represents $(C_1-C_4)$-alkyl.

$R^3$ preferably represents hydrogen, amino, chlorine, bromine, iodine or represents one of the following groupings:

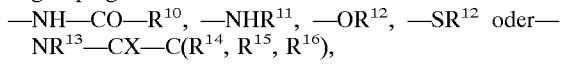

where
$R^{10}$ preferably represents $(C_1-C_4)$-alkyl, $(C_1-C_4)$-halogenoalkyl having 1 to 5 halogen atoms, $(C_1-C_4)$-alkoxy-$(C_1-C_4)$-alkyl or represents phenyl, phenoxy or pyridyl, each of which is optionally mono- to pentasubstituted by identical or different substituents, possible substituents being the phenyl substituents already mentioned above for $R^2$, $R^{11}$ preferably represents $(C_1-C_4)$-alkyl, $(C_2-C_4)$-alkenyl, $(C_2-C_4)$-alkinyl, formyl, $(C_1-C_4)$-alkyl-carbonyl, $(C_1-C_4)$-halogenoalkyl-carbonyl having 1 to 5 halogen atoms or $(C_1-C_4)$-alkoxy-carbonyl, $R^{12}$ preferably represents $(C_1-C_4)$-alkyl, $(C_2-C_4)$-alkenyl, $(C_2-C_4)$-alkinyl, di-$(C_1-C_4)$-alkylamino-$(C_1-C_4)$-alkyl; phenyl-$(C_1-C_2)$-alkyl which is optionally mono- to pentasubstituted by identical or different substituents, possible substituents being the phenyl substituents already mentioned above for $R^2$; or represents the grouping —P(=Y)(O$R^{17}$)(S$R^{18}$), where
$R^{17}$ and $R^{18}$ independently of one another preferably represent $(C_1-C_4)$-alkyl and
Y represents oxygen or sulphur, $R^{13}$ preferably represents hydrogen, $(C_1-C_4)$-alkyl, $(C_1-C_4)$-alkoxy-$(C_1-C_4)$-alkyl, propargyl, allyl, $(C_1-C_4)$-alkoxy-carbonyl, $(C_1-C_4)$-alkyl-carbonyl, represents benzyl which is optionally mono- to pentasubstituted by identical or different substituents, possible substituents being the phenyl substituents already mentioned above for $R^2$,
or represents the grouping —CO—C($R^{14}$, $R^{15}$, $R^{16}$), $R^{14}$ preferably represents hydrogen, $(C_1-C_4)$-alkyl, halogen, $(C_1-C_4)$-halogenoalkyl having 1 to 5 carbon atoms or represents phenyl which is optionally mono- to pentasubstituted by identical or different substituents, possible substituents being the phenyl substituents already mentioned above for $R^2$, $R^{15}$ preferably represents hydrogen, $(C_1-C_4)$-alkyl, halogen, $(C_1-C_4)$-halo-genoalkyl and $(C_1-C_4)$-halogenoalkoxy-$(C_1-C_4)$-alkyl having in each case 1 to 5 halogen atoms, $(C_1-C_4)$-alkylthio-$(C_1-C_4)$-alkyl, $(C_1-C_4)$-alkylsulphinyl-$(C_1-C_4)$-alkyl, $(C_1-C_4)$-alkylsulphonyl-$(C_1-C_4)$alkyl, $(C_1-C_4)$-alkoxy-[$(C_1-C_4)$-alkoxy]$_r$-$(C_1-C_4)$-alkyl where r=0 to 2, hydroxyl, $(C_1-C_4)$-alkoxy-carbonyl-$(C_1-C_4)$-alkyl and $(C_1-C_4)$-alkoxy, or $R^{14}$ and $R^{15}$ together with the carbon atom to which they are attached preferably represent a 5- to 6 or 7-membered ring system which may optionally contain up to two identical or different heteroatoms, such as O, S or N atoms, $R^{16}$ preferably represents hydroxyl, $(C_1-C_4)$-alkoxy, $(C_1-C_4)$-halogeno-alkoxy having 1 to 5 halogen atoms or $(C_1-C_4)$-alkoxy-[$(C_{1-4})$-alkoxy]$_q$where q=1 or 2, X preferably represents oxygen or sulphur.

Ar preferably represents phenyl or pyridyl, each of which is optionally mono- to trisubstituted by identical or different substituents, possible substituents being in each case the phenyl substituents already mentioned above for $R^2$.

$R^2$ particularly preferably represents $(C_1-C_4)$-alkyl, $(C_2-C_4)$-alkenyl, $(C_2-C_4)$-alkinyl, cyano-$(C_1-C_2)$-alkyl, thiocyanato-$(C_1-C_2)$-alkyl, nitro-$(C_1-C_2)$-alkyl, $(C_1-C_4)$-alkylthio-$(C_1-C_2)$-alkyl, $(C_{1-4})$-alkylsulphinyl-$(C_1-C_2)$-alkyl, $(C_1-C_4)$-alkylsulphonyl-$(C_1-C_2)$-alkyl, $(C_1-C_2)$-halogenoalkylthio-$(C_1-C_2)$-alkyl having 1 to 5 identical or different halogen atoms from the group consisting of fluorine, chlorine and bromine, $(C_1-C_2)$-halogenoalkyl-sulphinyl-$(C_1-C_2)$-alkyl and $(C_1-C_2)$-halogenoalkylsulphonyl-$(C_1-C_2)$-alkyl having in each case 1 to 5 identical or different halogen atoms from the group consisting of fluorine, chlorine and bromine, $(C_2-C_4)$-alkenylthio-$(C_1-C_2)$-alkyl, $(C_2-C_4)$-alkinylthio-$(C_1-C_2)$-alkyl, $(C_1-C_2)$-alkoxy-carbonyl-$(C_1-C_2)$-alkyl, $(C_1-C_2)$-halogenoalkoxy-carbonyl-$(C_1-C_2)$-alkyl having 1 to 5 identical or different halogen atoms from the group consisting of fluorine, chlorine and bromine, $(C_1-C_4)$-alkoxy-carbonyl, $(C_1-C_4)$-alkyl-carbonyl, $(C_1-C_4)$-alkoxy-$(C_1-C_2)$-alkyl, $(C_1-C_2)$-alkoxy-$(C_1-C_2)$-alkylthio-$(C_{1-2})$-alkyl, $(C_1-C_2)$-halogenoalkoxy-$(C_1-C_2)$-alkylthio-$(C_1-C_2)$-alkyl having 1 to 5 identical or different halogen atoms from the group consisting of fluorine, chlorine and bromine, $(C_1-C_2)$-alkylamino-$(C_1-C_2)$-alkyl, di-$(C_1-C_2)$-alkylamino- ($C_1$–$C_2$)-alkyl; represents cyclopropyl, cyclopentyl and cyclohexyl, each of which is optionally mono- to trisubstituted by identical or different substituents, possible substituents being:

methyl, ethyl, methoxy, ethoxy, fluorine, chlorine, bromine, trifluoromethyl and trifluoromethoxy; and represents phenyl, benzyl, phenoxymethyl, phenoxyethyl, phenylthiomethyl, phenylthioethyl, benzyloxymethyl, benzylthiomethyl, pyridyl or pyridylmethyl, each of which is optionally mono- to trisubstituted by identical or different substituents, possible phenyl or pyridyl substituents being: fluorine, chlorine, bromine, ($C_1$–$C_4$)-alkyl, allyl, ($C_1$–$C_4$)-alkoxy, allyloxy, ($C_1$–$C_2$)-alkylthio; ($C_1$–$C_2$)-halogenoalkyl or ($C_1$–$C_2$)-halogenoalkoxy or ($C_1$–$C_2$)-halogenoalkylthio having in each case 1 to 5 identical or different halogen atoms from the group consisting of fluorine, chlorine and bromine; cyano, nitro, hydroxyl, hydrazino, dimethylhydrazino, amino, methylamino, dimethylamino, iminomethyl, ($C_1$–$C_2$)-alkyl-carbonyl, ($C_1$–$C_2$)-alkyl-carbonyloxy; phenyl or phenoxy, each of which is optionally mono- to disubstituted by identical or different substituents from the group consisting of fluorine, chlorine, bromine, methyl, ethyl, methoxy, trifluoromethyl, trifluoromethoxy and trifluoromethylthio; $SF_5$ or the grouping

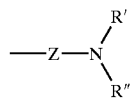

where
R' and R" independently of one another represent hydrogen or ($C_1$–$C_4$)-alkyl and
Z represents —CO or —$SO_2$, $R^2$ for m=0 additionally particularly preferably represents SCN, chlorine, iodine, nitro, cyano, hydroxyl, chlorosulphonyl, ($C_1$–$C_2$)-alkoxy, allyloxy, ($C_1$–$C_2$)-halogenoalkyl or ($C_1$–$C_2$)-halogenoalkoxy having in each case 1 to 5 identical or different halogen atoms from the group consisting of fluorine, chlorine and bromine; ($C_1$–$C_2$)-alkyl-carbonyloxy, formyl, —C≡C—Si($CH_3$)$_3$; represents phenoxy which is optionally mono- to disubstituted by identical or different substituents, possible substituents being the substituents already mentioned above for $R^2$; further represents —CONHF$_2$, —CSNH$_2$, —CON(CH$_3$)$_2$, —CON(C$_2$H$_5$)$_2$, —CH=NOCH$_3$, —CH=NOC$_2$H$_5$, —C(CH$_3$)=NOCH$_3$ and —CH(OH)CF$_3$.

$R^3$ particularly preferably represents hydrogen, amino, chlorine, ($C_1$–$C_4$)-alkylamino and also represents the grouping —NH—CO—$R^{10}$,
where
$R^{10}$ particularly preferably represents ($C_1$–$C_4$)-alkyl, ($C_1$–$C_2$)-haloalkyl having 1 to 5 identical or different halogen atoms from the group consisting of fluorine, chlorine and bromine and also represents phenyl and phenoxy, each of which is optionally mono- to disubstituted by identical or different substituents, possible substituents being the phenyl substituents already mentioned above for $R^2$ and Ar particularly preferably represents phenyl or pyridyl, each of which is optionally mono- to trisubstituted by identical or different substituents from the group consisting of fluorine, chlorine, bromine; ($C_1$–$C_2$)-halogenoalkyl and ($C_1$–$C_2$)-halogenoalkoxy and ($C_1$–$C_2$)-halogenoalkylthio and ($C_1$–$C_2$)-halogenoalkylsulphinyl and ($C_1$–$C_2$)-halogenoalkylsulphonyl having in each case 1 to 5 identical or different halogen atoms from the group consisting of fluorine, chlorine and bromine; ($C_1$–$C_2$)-alkyl, ($C_1$–$C_2$)-alkoxy, hydrazino, dimethylhydrazino, amino, methylamino, dimethylamino, cyano, $SF_5$ or the grouping

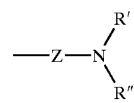

where
R' and R" independently of one another represent hydrogen or ($C_1$–$C_4$)-alkyl and
Z represents CO or $SO_2$.

$R^2$ very particularly preferably represents $CH_3$, $C_2H_5$, —CH$_2$—CH=CH$_2$, —C≡CH, —CH$_2$-C≡CH, —CH$_2$—CN, —CH$_2$-SCN, —CH$_2$-NO$_2$, —CH$_2$—S—CH$_3$, —CH$_2$—S—C$_2$H$_5$, —CH$_2$CH$_2$—S—CH$_3$, —CH$_2$CH$_2$—S—C$_2$H$_5$, —CH$_2$—SO—C$_2$H$_5$, —CH$_2$—SO$_2$—C$_2$H$_5$, —CH$_2$—S—CF$_3$, CH$_2$—SO—CF$_3$, CH$_2$-SO$_2$—CF$_3$, —CH$_2$—S—CH$_2$—CH=CH$_2$, —CH$_2$—S—CH$_2$—C≡—CH, —CH$_2$—CO—OCH$_3$, —CH$_2$—CO—OC$_2$H$_5$, —(CH$_2$)$_2$—CO—OCH$_3$, —(CH$_2$)$_2$—CO—OC$_2$H$_5$, —CH$_2$—CO—OCF$_3$, —CO—OCH$_3$, —CO—OC$_2$H$_5$, —CO—CH$_3$, —CO—C$_2$H$_5$, —CH$_2$—OCH$_3$, —CH$_2$—OC$_2$H$_5$, —CH$_2$—S—CH$_2$CH$_2$—O—C$_2$H$_5$, —CH$_2$—S—CH$_2$CH$_2$—O—CH$_2$CF$_3$, —CH$_2$—NHC$_2$H$_5$, —CH$_2$CH$_2$—N(CH$_3$)$_2$, —CH$_2$CH$_2$—N(C$_2$H$_5$)$_2$, cyclopropyl, and represents benzyl, benzyloxymethyl, benzylthiomethyl, phenoxymethyl, phenoxyethyl, phenylthiomethyl or phenylthioethyl, each of which is optionally mono- to trisubstituted by identical or different substituents, possible phenyl substituents being in each case:

fluorine, chlorine, trifluoromethyl, trifluoromethoxy, trifluoromethylthio, methoxy, hydrazino, dimethylhydrazino, amino, methylamino, dimethylamino, cyano, methylthio, —CONH$_2$, —CSNH$_2$, phenyl, chlorophenyl, fluorophenyl, dichlorophenyl, phenoxy, chlorophenoxy, fluorophenoxy and dichlorophenoxy, $R^2$ for m=0 additionally very particularly preferably represents SCN, chlorine, iodine, nitro, cyano, —OCH$_3$, —CF$_3$, —OCF$_3$, —O—COCH$_3$,

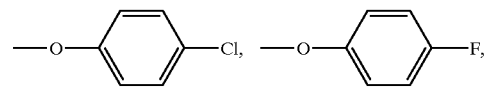

—CSNH$_2$, —CON(CH$_3$)$_2$, —CH=NOCH$_3$ and —CH(OH)CF$_3$, $R^3$ very particularly preferably represents hydrogen, amino, chlorine, —NHCH$_3$,

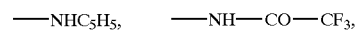

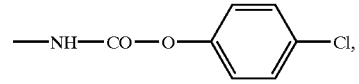

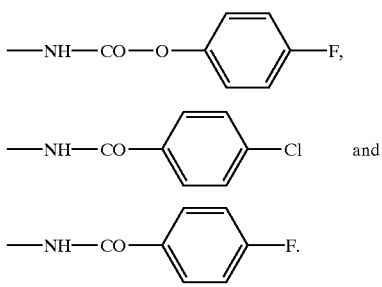

Ar very particularly preferably represents phenyl or 2-pyridyl, each of which is di- or trisubstituted by identical or different substituents from the group consisting of F, Cl, Br, $CF_3$, $OCF_3$, $SCF_3$, $SOCF_3$, $SO_2CF_3$, $OCH_2CF_3$, $CH_3$ and $SF_5$.

The abovementioned or preferred radical definitions or illustrations apply to the end products and correspondingly to the starting materials and intermediates. These radical definitions can be combined with one another as desired, i.e. including combinations between the respective preferred ranges.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

In the radical definitions listed above and below, hydrocarbon radicals, such as alkyl or alkenyl, are in each case straight-chain or branched as far as this is possible—including in compounds with heteroatoms, such as in alkoxy or alkylthio.

Preference is given to compounds of the formulae (IA-1) to (IA-5):

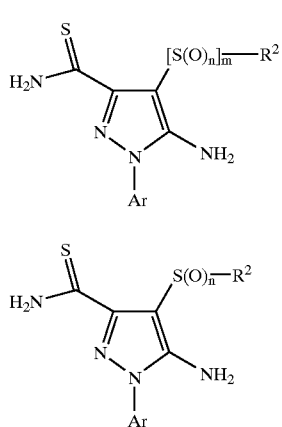

(IA-1)

(IA-2)

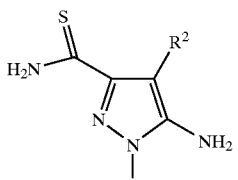

(IA-3)

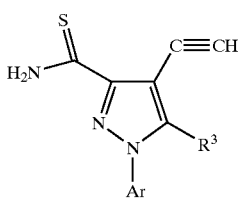

(IA-4)

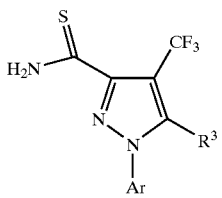

(IA-5)

in which

Ar, $R^2$, $R^3$, m and n have the general, preferred, particularly preferred and very particularly preferred meanings mentioned above.

Examples of the novel substituted 3-thiocarbamoylpyrazoles are listed in Tables 1 to 14:

TABLE 1

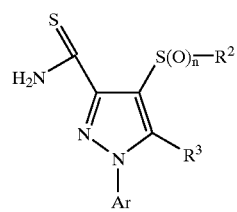

(IB)

Compounds of Table 1 correspond to the general formula (IB) in which for

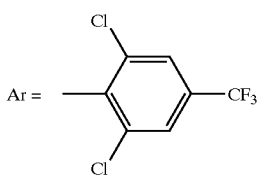

the following combinations of substituents apply:

| R² | n | R³ |
|---|---|---|
| CH₃ | 0 | NH₂ |
| CH₃ | 1 | NH₂ |
| CH₃ | 1 | NHC₂H₅ |
| C₂H₅ | 2 | NH₂ |
| C₂H₅ | 2 | NHC₂H₅ |
| C₂H₅ | 1 | NH—COCF₃ |
| C₂H₅ | 1 | 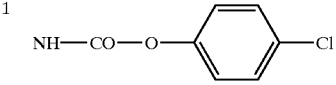 NH—CO—O—C₆H₄—Cl |
| —CH₂—SCF₃ | 1 | NH₂ |
|  cyclopropyl | 1 | NH₂ |
| —CH₂—S—CH₂—C₆H₄—Cl | 1 | NH₂ |
| —CH₂—CN | 1 | NH₂ |
| —CH₂—NO₂ | 0 | NH₂ |
| —CH₂—S—CF₃ | 0 | H |
| —CH₂—S—CF₃ | 0 | Cl |
| —CH₂—S—C₂H₅ | 1 | NH₂ |
| —CO—O—C₂H₅ | 0 | H |
| —CH₂—O—C₂H₅ | 1 | NH₂ |
| —CH₂CH₂—N(C₂H₅)₂ | 2 | NH₂ |
| —CH₂—C≡CH | 1 | NH₂ |
| —CH₂—CH=CH₂— | 1 | NH₂ |
| —CH₂—SO—CF₃ | 1 | NH₂ |
| —CH₂—S—CH₂—CH=CH₂ | 1 | NH₂ |
| —CH₂—S—CH₂—C≡CH | 1 | NH₂ |
| —CH₂—CO—OCF₃ | 1 | NH₂ |
| —CH₂—S—CH₂CH₂—O—CH₂CF₃ | 1 | NH₂ |
| —CH₂CH₂—S—CH₃ | 0 | NHCH₃ |
| —CH₂—SCN | 0 | NH₂ |
| —CH₂—SO₂—C₂H₅ | 2 | NH₂ |
| —CO—OCH₃ | 1 | NH₂ |
| —CH₂—S—C₆H₄—Cl | 0 | NH₂ |
| —CH₂CH₂—S—C₂H₅ | 0 | NH₂ |

TABLE 2

Table 2 contains compounds of the general formula (IB) in which

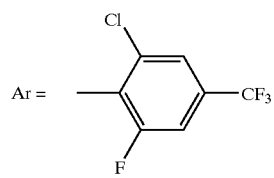

Ar = (2-Cl, 6-F, 4-CF₃ phenyl)

and the combinations of substituents listed in Table 1 apply to R², n and R³.

TABLE 3

Table 3 contains compounds of the general formula (IB) in which

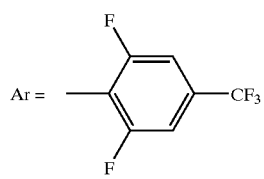

Ar = (2-F, 6-F, 4-CF₃ phenyl)

and the combinations of substituents listed in Table 1 apply to R², n and R³.

TABLE 4

Table 4 contains compounds of the general formula (IB) in which

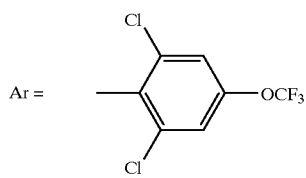

and the combinations of substituents listed in Table 1 apply to $R^2$, n and $R^3$.

TABLE 5

Table 5 contains compounds of the general formula (IB) in which

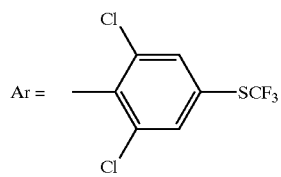

and the combinations of substituents listed in Table 1 apply to $R^2$, n and $R^3$.

TABLE 6

Table 6 contains compounds of the general formula (IB) in which

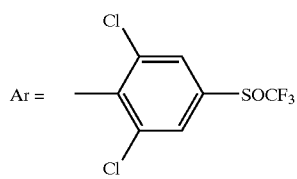

and the combinations of substituents listed in Table 1 apply to $R^2$, n and $R^3$.

TABLE 7

Table 7 contains compounds of the general formula (IB) in which

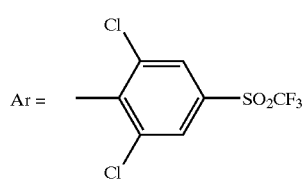

TABLE 7-continued and the combinations of substituents listed in Table 1 apply to $R^2$, n and $R^3$.

TABLE 8

Table 8 contains compounds of the general formula (IB) in which

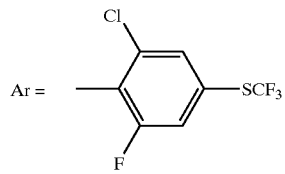

and the combinations of substituents listed in Table 1 apply to $R^2$, n and $R^3$.

TABLE 9

Table 9 contains compounds of the general formula (IB) in which

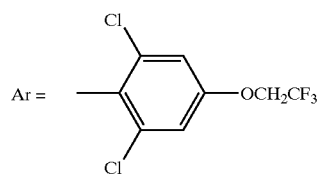

and the combinations of substituents listed in Table 1 apply to $R^2$, n and $R^3$.

TABLE 10

Table 10 contains compounds of the general formula (IB) in which

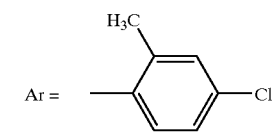

and the combinations of substituents listed in Table 1 apply to $R^2$, n and $R^3$.

TABLE 11

Table 11 contains compounds of the general formula (IB) in which

Ar = 2,6-dichloro-4-(SF$_5$)phenyl and the combinations of substituents listed in Table 1 apply to $R^2$, n and $R^3$.

TABLE 12

Table 12 contains compounds of the general formula (IB) in which

Ar = 2,6-dichloro-4-bromophenyl and the combinations of substituents listed in Table 1 apply to $R^2$, n and $R^3$.

TABLE 13

Compounds of Table 13 correspond to the general formula (IB) in which for

Ar = 3-chloro-5-(trifluoromethyl)pyridin-2-yl the following combinations of substituents apply:

| $R^2$ | n | $R^3$ |
|---|---|---|
| CH$_3$ | 0 | NH$_2$ |
| CH$_3$ | 1 | NH$_2$ |
| CH$_3$ | 1 | NHC$_2$H$_5$ |
| C$_2$H$_5$ | 2 | NH$_2$ |
| C$_2$H$_5$ | 2 | NHC$_2$H$_5$ |
| C$_2$H$_5$ | 1 | NH—COCF$_3$ |
| C$_2$H$_5$ | 1 | NH—CO—O—(4-Cl-C$_6$H$_4$) |
| —CH$_2$—SCF$_3$ | 1 | NH$_2$ |
| cyclopropyl | 2 | NH$_2$ |
| —CH$_2$—S—CH$_2$—(4-Cl-C$_6$H$_4$) | 1 | NH$_2$ |
| —CH$_2$—CN | 1 | NH$_2$ |
| —CH$_2$—NO$_2$ | 0 | NH$_2$ |
| —CH$_2$—SCF$_3$ | 0 | H |

TABLE 14

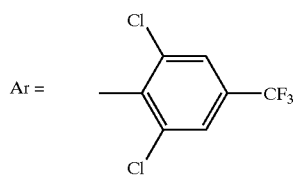
(IC)

Compounds of Table 14 correspond to the general formula (IC) in which for

Ar = [2,6-dichloro-4-trifluoromethylphenyl]

the following combinations of substituents apply:

| R² | R³ |
|---|---|
| —C≡CH | NH₂ |
| CF₃ | NH₂ |
| I | NH₂ |
| —CH=NOCH₃ | NH₂ |
| —OCF₃ | NH₂ |
| —C≡C—Si(CH₃)₃ | NH₂ |
| —C≡CH | NH—COCH₃ |
| —C≡CH | NH—C₂H₅ |
| —SCN | NH₂ |
| —C≡CH | NH—CO—CF₃ |
| —C≡CH | NH—CO—C₆H₄—Cl |
| —NO₂ | NH₂ |
| —NO₂ | Cl |
| —C≡CH | Cl |
| —C≡CH | H |
| —CH₃ | NH₂ |
| C₂H₅ | NH₂ |
| —OCH₃ | NH₂ |
| —CO—N(CH₃)₂ | NH₂ |
| —CH(OH)CF₃ | NH₂ |
| —CS—NH₂ | NH₂ |
| —O—COCH₃ | NH₂ |
| —SO₂Cl | NH₂ |

Using, for example, 5-amino-3-cyano-4-(ethylthio)-1-(2,6-dichloro-4-trifluoromethylphenyl)-pyrazole and hydrogen sulphide as starting materials, the course of the reaction of the process (a) according to the invention can be represented by the following equation:

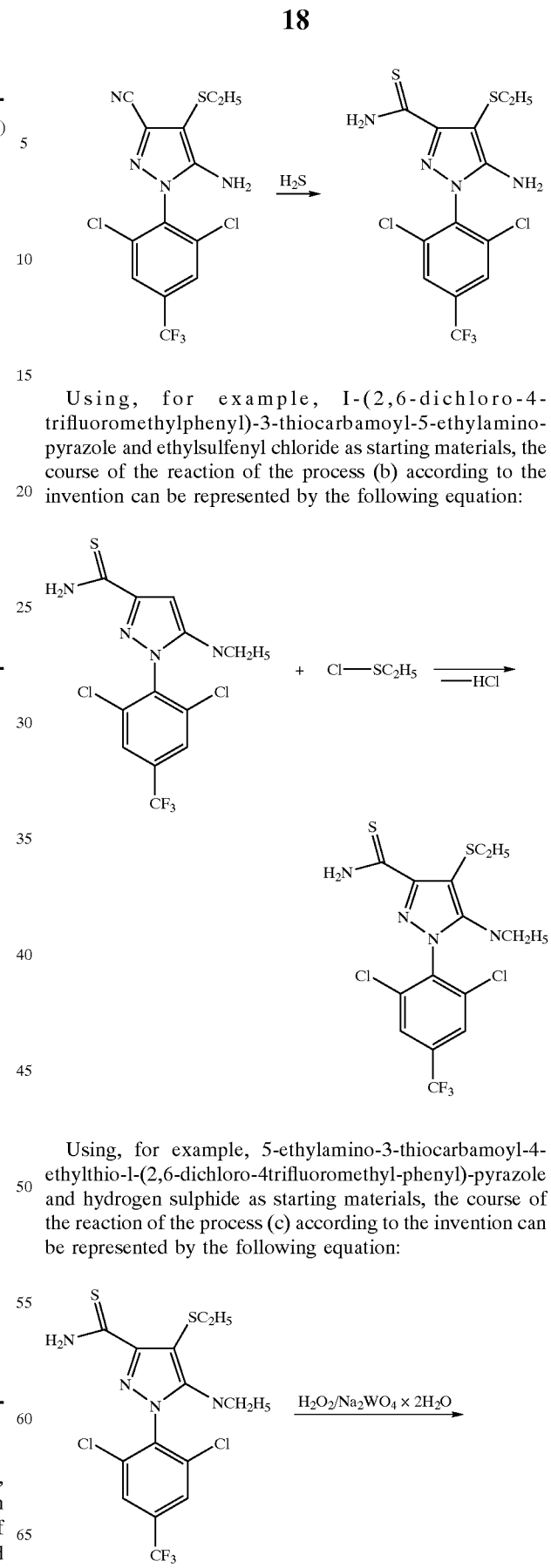

Using, for example, 1-(2,6-dichloro-4-trifluoromethylphenyl)-3-thiocarbamoyl-5-ethylamino-pyrazole and ethylsulfenyl chloride as starting materials, the course of the reaction of the process (b) according to the invention can be represented by the following equation:

Using, for example, 5-ethylamino-3-thiocarbamoyl-4-ethylthio-1-(2,6-dichloro-4trifluoromethyl-phenyl)-pyrazole and hydrogen sulphide as starting materials, the course of the reaction of the process (c) according to the invention can be represented by the following equation:

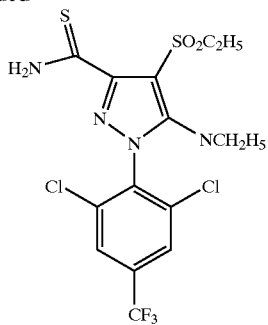

The 3-cyanopyrazole derivatives of the formula (II) to be used as starting materials for carrying out the process (a) according to the invention are known (cf., for example, EP 0 295 117, GB 2 308 365, WO 98/04 530 and WO 97/07 102) and/or can be prepared analogously to known processes.

The 3-thiocarbamoylpyrazole derivatives of the formula (III) to be used as starting materials for carrying out the process (b) according to the invention are novel, and some of them form part of the subject-matter of an earlier application of the applicant (cf. German patent application 196 50 197 dated Apr. 12,1996).

The compounds of the formula (III) can be obtained by reacting 2-cyanopyrazoles of the formula (V):

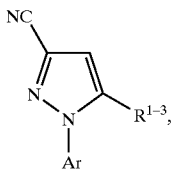

in which

Ar and $R^{3-1}$ arc as defined above, according to the process (a) according to the invention with hydrogen sulphide, if appropriate in the presence of a reaction auxiliary and if appropriate in the presence of a diluent.

The 3-cyanopyrazoles of the formula (V) are known (cf., EP 659 745), and/or they can be obtained by generally customary processes.

The sulphenyl halides of the formula (IV) furthermore to be used as starting materials for the process (b) according to the invention are generally known compounds of organic chemistry, and/or can be prepared by known processes.

The 3-thiocarbamoylpyrazole derivatives of formula (Ia) to be used as starting materials for the process (c) according to the invention are compounds according to the invention.

The process (a) according to the invention is preferably carried out using a diluent. Suitable diluents are virtually all inert organic solvents. These preferably include aliphatic and aromatic, optionally halogenated hydrocarbons, such as pentane, hexane, heptane, cyclohexane, petroleum ether, benzine, ligroine, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone or methyl isobutyl ketone, esters, such as methyl acetate or ethyl acetate, nitriles, such as, for example, acetonitrile or propionitrile, amides, such as, for example, dimethylformamide, dimethylacetamide and N-methylpyrrolidone, and also dimethyl sulphoxide, tetramethylene sulphone or hexamethylenephosphoric triamide.

Suitable for use as reaction auxiliaries in the process (a) according to the invention are all bases which can customarily be used for such reactions. Preference is given to using basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethylaniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4.3.0]-non-5-ene (DBN), 1,8-diazabicyclo-[5.4.0]-undec-7-ene (DBU) or 1,4-diazabicyclo-[2.2.2]-octane (DABCO). It is also possible to use an excess of reaction auxiliary as diluent.

In the process (a) according to the invention, the reaction temperatures can be varied within a relatively wide range. In general, the process is carried out at temperatures between 0° C. and 100° C., preferably at temperatures between 10° C. and 80° C.

The process (a) according to the invention is generally carried out under atmospheric pressure. However, it is also possible to operate under elevated or reduced pressure.

For carrying out the process (a) according to the invention, the hydrogen sulphide is generally employed in excess. The reactions are generally carried out in a suitable diluent in the presence of a basic nitrogen compound. Work-up is carried out by customary methods (cf. the Preparation Examples).

Suitable diluents for carrying out the process (b) according to the invention are inert organic solvents. These include in particular aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride; ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile; amides, such as dimethylformamide, dimethylacetamide, N-methylformanilide, N-methylpyrrolidone or hexamethylphosphoric triamide, esters, such as ethyl acetate, sulphoxides, such as dimethyl sulphoxide, or acids, such as, for example, acetic acid.

If appropriate, the process (b) according to the invention can be carried out in the presence of a reaction auxiliary. Suitable reaction auxiliaries are all customary inorganic or organic bases. These include, for example, alkali metal hydroxides, such as sodium hydroxide or potassium hydroxide, alkali metal carbonates or bicarbonates, such as sodium carbonate, potassium carbonate or sodium bicarbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

When carrying out the process (b) according to the invention, the reaction temperatures can be varied within a relatively wide range. In general, the process is carried out at temperatures between −20° C. and +120° C., preferably at temperatures between 0° C. and +50° C.

For carrying out the process (b) according to the invention, in general from 1.0 to 2.5 mol, preferably from 1.0 to 1.5 mol, of sulphenyl halide of the formula (IV) and, if appropriate, from 1.0 to 2.5 mol, preferably from 1.0 to 1.5 mol, of reaction auxiliary are employed per mole of 4-substituted 1-arylpyrazole of the formula (III). The practice of the reaction and the work-up and isolation of the reaction products is carried out by generally customary processes.

Suitable oxidizing agents for carrying out the process (c) according to the invention are all oxidizing agents which are customarily used for sulphur oxidation. Particularly suitable are hydrogen peroxide, organic peracids, such as, for example, peracetic acid, m-chloroperbenzoic acid, p-nitroperbenzoic acid or atmospheric oxygen.

Suitable diluents for carrying out the process (c) according to the invention are likewise inert organic solvents. Preference is given to using hydrocarbons, such as benzine, benzene, toluene, hexane or petroleum ether; chlorinated hydrocarbons, such as dichloromethane, 1,2-dichlorethane, chloroform, carbon tetrachloride or chlorobenzene; ethers, such as diethyl ether, dioxane or tetrahydrofuran; carboxylic acids, such as acetic acid or propionic acid, or dipolar aprotic solvents, such as acetonitrile, acetone, ethyl acetate or dimethyl formamide.

If appropriate, the process (c) according to the invention can be carried out in the presence of an acid binder. Suitable acid binders are all organic and inorganic acid binders which are customarily used. Preference is given to using alkaline earth metal or alkali metal hydroxides, acetates or carbonates, such as, for example, calcium hydroxide, sodium hydroxide, sodium acetate or sodium carbonate.

If appropriate, the process (c) according to the invention can be carried out in the presence of a suitable catalyst. Suitable catalysts are all metal salt catalysts which are customarily used for such sulphur oxidations. Examples which may be mentioned are ammonium molybdate and sodium tungstate.

When carrying out the process (c) according to the invention, the reaction temperatures can be varied within a relatively wide range. In general, the process is carried out at temperatures between −20° C. and +7° C., preferably at temperatures between 0° C. and +50° C.

For carrying out the process (c) according to the invention, in general from 0.8 to 1.2 mol, preferably equimolar amounts, of oxidizing agent are employed per mole of the compound of the formula (Ia) if the oxidation of the sulphur is to be interrupted at the sulphoxide stage. For oxidation to the sulphone, in general from 1.8 to 3.0 mol, preferably twice the molar amount, of oxidizing agent is employed per mole of the compound of the formula (Ia). The practice of the reaction and the work-up and isolation of the end products are carried out by customary processes.

Substituted 3-thiocarbamoylpyrazoles of the formula (Ia) according to the invention can optionally also be obtained by reacting 3-thiocarbamoyl-4-thiocyanato-pyrazoles of the formula (Ib):

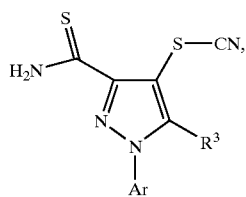

(Ib)

in which
Ar and R³ are as defined above
with halides of the formula (VI):

Hal-R² (VI), in which
Hal and R² are as defined above
in a generally customary manner in the presence of a diluent, such as in particular an alcohol (preferably ethanol)/water mixture, at temperatures between −80° C. and 50° C., preferably between −50° C. and room temperature, where the halide of the formula (VI) is preferably employed in an equimolar amount, if appropriate also in a slight excess.

The active compounds are suitable for controlling animal pests, in particular insects, arachnids and nematodes, which are encountered in agriculture, in forestry, in the protection of stored products and of materials, and in the hygiene field, and have good plant tolerance and favorable toxicity to warm-blooded animals. They may be preferably employed as plant protection agents. They are active against normally sensitive and resistant species and against all or some stages of development. The abovementioned pests include:

From the order of the Isopoda, for example, *Oniscus asellus*, *Arnadillidium vulgare* and *Porcellio scaber*.

From the order of the Diplopoda, for example, *Blaniulus guttulatus*.

From the order of the Chilopoda, for example, *Geophilus carpophagus* and Scutigera spec.

From the order of the Symphyla, for example, *Scutigerella immaculata*.

From the order of the Thysanura, for example, *Lepisma saccharina*.

From the order of the Collembola, for example, Onychiurus armatus.

From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria*.

From the order of the Dermaptera, for example, *Forficula auricularia*.

From the order of the Isoptera, for example, Reticulitermes spp.

From the order of the Anoplura, for example, *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorunm, Aphis gossypii, Brevicoryne brassicae, Cryptomyzus ribis, Aphis fabae, Aphis pomi, Eriosoma lanigerum, Hyalopterus arundinis, Phylloxera vastatrix*, Pemphigus spp., *Macrosiphum avenae*, Myzus spp., *Phorodon humuli, Rhopalosiphum padi*, Empoasca spp., *Euscelis bilobatus, Nephotettix cincticeps, Lecanium comi, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculiperinis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Spodoptera litura*, Spodoptera spp., *Trichoplusia ni, Carpocapsa pomonella*, Pieris spp., Chilo spp., *Pyrausta nubilalis, Ephestia*

*kuehniella, Galleria mellonella, Tineola bisselliella, Tinea pellionella, Hofinannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chlrysocephala, Epilachna varivestis,* Atomaria spp., *Oryzaephilus Surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomoriurn pharaonis* and Vespa spp:

From the order of the Diptera, for example, Aedes spp., Anopheles spp., Culex spp., *Drosophila melanogaster,* Musca spp., Fannia spp., *Calliphora erythrocephala, Lucilia* spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyani, Ceratitis capitata, Dacus oleae* and *Tipula paludosa*.

From the order of the Siphonaptera, for example, *Xenopsylla cheopis* and Ceratopliyllus spp.

From the order of the Arachnida, for example, *Scorpio maurus* and *Latrodectus mactans*.

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include, for example, Pratylenchus spp., *Radopholus sinimilis, Ditylenchus dipsaci, Tylenchulus semipenetrans,* Heterodera spp., Globodera spp., Meloidogyne spp., Aphelenchoides spp., Longidorus spp., Xiphinema spp. and Trichodorus spp.

The compounds of the formula (I) according to the invention are distinguished in particular by a high insecticidal activity. They can be employed particularly successfully for controlling phytopathogenic insects, such as, for example, against caterpillars of the owlet moth (*Spodoptera frugiperda*) and the green peach aphid (*Myzus persicae*).

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is, liquid solvents, and/or solid carriers, optionally with the use of surfactants, that is emulsifiers and/or dispersants, and/or foam-forming agents.

If the extender used is water, it is also possible to employ for example organic solvents as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water.

As solid carriers there are suitable: for example ammonium salts and ground natural minerals, such as kaolins, clays, talc, chalk, quartz, attapulgite, moritmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersing agents there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of co-components in mixtures are the following compounds:

Fungicides:

aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenftiram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulphamide, flutolanil, flutriafol, folpet, fosetyl-aluminium, fosetyl-sodium, fthalide, fuberidazole, furalaxyl, furametpyr, furcarbonil, furconazole, fuirconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulphocarb, methfuroxam, metiram, metomeclam, metsulphovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol, α-(2,4-dichlorophenyl)-β-fluoro-β-propyl-1H-1,2,4-triazole-1-ethanol, α-(2,4-dichlorophenyl)-β-methoxy-β-methyl-1H-1,2,4-triazole-1-ethanol, α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, isopropyl{2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-5 carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glucopyranosyl)-α-D-glucopyranosyl]-amino]-4-methoxy-1H-pyrrolo[2,3-d] pyrimidine-5-carbonitrile, 2-aminobutane, 2-bromo-2-(bromomethyl)-pentanedinitrile, 2-chloro-N-(2,3-dihydro-1, 1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2, 5-dione, 3,5-dichloro-N-[cyano-[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5] decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1₁-dimethylpropyl)-phenyl-2-methylpropyl]-2,6-dimethyl-morpholine hydrochloride, ethyl[(4-chlorophenyl)-azo]-cyanoacetate, potassium hydrogen carbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2, 6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidinamine, N-(4-hexylphenyl)-1 ,4,5,6-tetrahydro-2-pyrimidinamine, N-(5-chloro-2-methylphenyl)-2-methoxy-N-(2-oxo-3-oxazolidinyl)-acetamide, N-((6-methoxy)-3-pyridinyl)-cyclopropanecarboxamide, N-[2,2,2-trichloro-1-[(chloroacetyl)-amino]-ethyl]-benzamide, N-[3-chloro-4,5-bis-(2-propinyloxy)-phenyl]-N'-methoxy-methanimidamide, N-formyl-N-hydroxy-DL-alanine-sodium salt, O,O-diethyl [2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, spiro[2H]-1-benzopyran-2, 1 '(3'H)-isobenzofuran]-3'-one.

Bactericides:

bronopol, dichlorophen, nitrapyrin, nickel dimethyldithiocarbamate, kasugamycin, octhilinon, furan-carboxylic acid, oxytetracycline, probenazole, streptomycin, tecloftalam, copper sulphate and other copper formulations.

Insecticides/Acaricides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezin, cyanophos, cycloprothrin, cyfluthrin, cyhalothrin, cyhexatin, cypermethrin, cyromazin, deltamethnin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucytirinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbaam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos,

RH 5992, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301 5302, zetamethrin.

A mixture with other known active compounds, such as herbicides or with fertilizers and growth regulators, is also possible.

The active compounds according to the invention can furthermore be present in their commercially available formulations and in the use forms, prepared from these formulations, as a mixture with synergistic agents when used as insecticide. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, Haematopinus spp., Linognathus spp., Pediculus spp., Phtirus spp. and Solenopotes spp.

From the order of the Mallophagida and the suborders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order of the Diptera and the suborders Nematocerina and Brachycerina, for example, Acdes spp., Anopheles spp., Culex spp., Simulium spp., Eusimulium spp., Phlebotonius spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypodenna spp., Gasterophilus spp., Hippobosca spp., Lipoptena spp. and Melophagus spp.

From the order of the Siphonapterida, for example Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example *Blatta orientalis, Periplaneta americana, Blattela germanica* and Supella spp.

From the subclass of the Acaria (Acarida) and the orders of the Meta- and Mesostigmata, for example, Argas spp., Ornithodorus spp., Otobius spp., Ixodes spp., Amblyomma spp., Boophilus spp., Dermacentor spp., Haemophysalis spp., Hyalomma spp., Rhipicephalus spp., Dermnanyssus spp., Raillietia spp., Pneumonyssus spp., Stemostoma spp. and Varroa spp.

From the order of the Actinedida (Prostigmata) und Acaridida (Astigmata), for example, Acarapis spp., Cheyletiella spp., Omithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

For example, they show good activity against flies (*Musca domestica*), development-inhibitory activity against fly larvae of *Lucilia cuprina* and a good activity against cat fleas (*Ctenocephalides felis*) and against ticks (*Boophilus microplus*), also in the form of an inhibition of oviposition.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10,000-fold dilution, or they can be used as a chemical bath.

It has furthermore been found that the compounds of the formula (I) according to the invention also have a potent insecticidal action against insects which destroy industrial materials.

The following insects may be mentioned as examples and as preferred—but without a limitation:

Beetles such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis*; Xyleborus spec., Tryptodendron spec., *Apate monachus, Bostrychus capucins, Heterobostrychus brunneus*, Sinoxylon spec., *Dinoderus minutus;*

Hynenopterons, such as *Sirex juvencus, Urocerus gigas, Urocerus gigas taignus, Urocerus augur;*

Termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccarina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agent according to the invention or mixtures comprising it are to be understood as meaning, for example: building timber, wooden beams, railway sleepers, bridge components, boat jetties, wooden vehicles, boxes, pallets, containers, telegraph poles, wood paneling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water-repellent, if appropriate siccative and UV stabilizers and if appropriate dyestuffs and pigments, and also other processing auxiliaries.

The insecticidal compositions or concentrates used for preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., test benzine having a boiling range from 170 to 220° C., spindle oil having a boiling range from 250 to 350° C, petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably (x-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, provided that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Very particularly preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The preparation and the use of the active compounds according to the invention are evident from the examples below.

PREPARATION EXAMPLES

Example 1

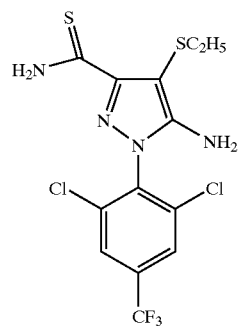

0.8 g (2.1 mmol) of 5-amino-3-cyano-4-ethylthio-1-(2,6-dichloro-4-trifluoromethyl-phenyl)-pyrazole (cf. EP 295 117) is dissolved in 30 ml of anhydrous pyridine and 2 ml of triethylamine. At room temperature, hydrogen sulphide is slowly introduced, the temperature rising to 28° C. After 60 minutes, the reaction has ended. The reaction mixture is concentrated and the crude product is purified by silica gel chromatography (cyclohexane/ethyl acetate 2/1).

This gives 0.4 g (46% of theory) of 5-amino-4-ethylthio-1-(2,6-dichloro-4-trifluoro-methylphenyl)-3-thiocarbamoyl-pyrazole of melting point 101° C.

The compounds of the formula (I) listed in Table A below are obtained analogously to Example 1 and/or in accordance with the general statements on the preparation:

TABLE A (I)

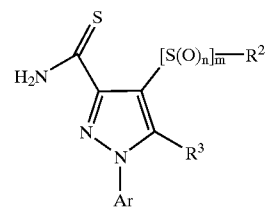

| Ex. No. | $[S(O)_n]_{\overline{m}}$—$R^2$ | $R^3$ | Ar | Physical const. |
|---|---|---|---|---|
| 2 | —SO—$C_2H_5$ | $NH_2$ | Cl, Cl, $CF_3$ substituted phenyl | m.p. 176° C. |

TABLE A-continued (I)

| Ex. No. | [S(O)ₙ]ₘ—R² | R³ | Ar | Physical const. |
|---|---|---|---|---|
| 3 | —S—CH₂S—C₆H₄—Cl (4-Cl) | NH₂ | 2,6-diCl-4-CF₃-phenyl | ¹H-NMR 9.69(1H); 9.10(1H); 8.22(2H); 7.47–7.35 (4H); 6.05(2H); 4.29(2H) |
| 4 | —S—(CH₂)₂SC₂H₅ | NH₂ | 2,6-diCl-4-CF₃-phenyl | ¹H-NMR 9.69(1H); 9.08(1H); 8.25(2H); 6.13(2H); 2.83–2.42(6H); 1.11(3H) |
| 5 | —S—(CH₂)₂O—C₆H₄—F (4-F) | NH₂ | 2,6-diCl-4-CF₃-phenyl | m.p. 168° C. |
| 6 | —S—(CH₂)₂O—C₆H₃—Cl₂ (2,4-diCl) | NH₂ | 2,6-diCl-4-CF₃-phenyl | ¹H-NMR 9.77(1H); 9.12(1H); 8.20(2H); 7.78(1H); 7.42–7.37(2H); 6.02 (2H); 4.11(2H); 3.12(2H) |
| 7 | —S—CH₂—C₆H₄—SCF₃ (4-SCF₃) | NH₂ | 2,6-diCl-4-CF₃-phenyl | ¹H-NMR 9.65(1H); 8.99(1H); 8.18(2H); 7.58–7.55 (2H); 7.40–7.37 (2H); 5.67(2H); 4.07(2H) |
| 8 | —CN | | 2,6-diCl-4-CF₃-phenyl | m.p. 170° C. |
| 9 | —CN | | 3-Cl-5-CF₃-pyridin-2-yl | m.p. 107° C. |

TABLE A-continued

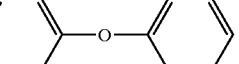

(I)

| Ex. No. | [S(O)$_n$]$_m$—R$^2$ | R$^3$ | Ar | Physical const. |
|---|---|---|---|---|
| 10 | 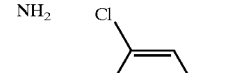 | NH$_2$ | 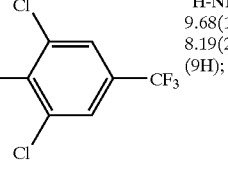 | $^1$H-NMR 9.68(1H); 8.98(1H); 8.19(2H); 7.41–6.85 (9H); 5.66(2H); 3.98(2H) |
| 11 | —CN | NH$_2$ | 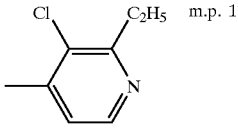 | m.p. 176° C. |
| 12 | —S—CH$_2$CH=CH$_2$ | NH$_2$ | 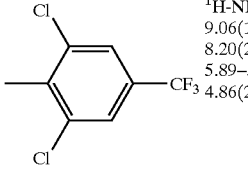 | $^1$H-NMR 9.06(1H); 9.04(1H); 8.20(2H); 5.91(2H); 5.89–5.78(1H); 4.91–4.86(2H); 3.38–3.35(2H) |
| 13 | —S—(CH$_2$)$_2$CO—OC$_2$H$_5$ | NH$_2$ | 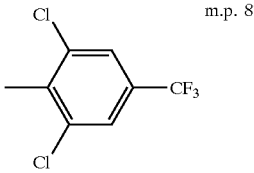 | m.p. 87° C. |

[$^1$H-NMR: in DMSO using TMS as internal standard, δ in ppm]

Use Examples

Example A

Myzus test

Solvent: 7 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

Cabbage leaves (*Brassica oleracea*) which are heavily infested by the green peach aphid (*Mycus persicae*) are treated by being dipped into the preparation of active compound of the desired concentration.

After the desired period of time, the kill in % is determined. 100% means that all aphids have been killed; 0% means that none of the aphids have been killed.

In this test, at an exemplary active compound concentration of 0.1%, the compound of Preparation Example 1, for example, shows a kill of 90% and the compounds of Preparation Examples 2 and 8 a kill of 100%, in each case after 6 days.

Example B

Spodoptera frugiperda test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbabe leaves (*Brassica oleracea*) are treated by being dipped into the preparation of active compound of the desired concentration and are populated with caterpillars of the army worm (*Spodoptera frugiperda*) while the leaves are still moist.

After the desired period of time, the kill in % is determined. 100% means that all caterpillars have been killed; 0% means that none of the caterpillars have been killed.

In this test the compound of Preparation Example 2, for example, showed a kill of 85% after 7 days at an exemplary active compound concentration of 0.1%.

Example C

Test with flies (*Musca domestica*)

Test animals: Adult *Musca domestica*, Reichswald strain (OP, SP, carbamate-resistant)

Solvent: Dimethyl sulphoxide 20 mg of active compound are dissolved in 1 ml of dimethyl sulphoxide, while dilute concentrations are prepared by dilution with dist. $H_2O$.

2 ml of this active compound preparation are pippetted on to filter paper discs (Ø 9.5 cm) in petri dishes of corresponding dimensions. After the filter discs have dried, 25 test animals are transferred into the petri dishes, which are then covered.

After 1, 3, 5, 24 and 48 hours, the activity of the active compound preparation is determined. 100% means that all flies have been killed; 0% means that none of the flies have been killed.

In this test the compound of Preparation Example 2, for example, showed an activity of 100% at an exemplary active compound concentration of 100 ppm.

Example D

Blowfly larvae test/development-inhibitory action

Test animals: *Lucilia cuprina* larvae

Solvent: Dimethyl sulphoxide 20 mg of active compound are dissolved in 1 ml of dimethyl sulphoxide, while dilute concentrations are prepared by dilution with dist. $H_2O$.

About 20 *Lucilia cuprina* larvae are introduced into a test tube containing about 1 $cm^3$ of horse meat and 0.5 ml of the preparation of active compound. After 24 and 48 hours, the activity of the preparation of active compound is determined. The test tubes are transferred into beakers whose bottom is covered with sand. After a further 2 days, the test tubes are removed and the pupae are counted.

The activity of the active compound preparation is assessed by the number of flies which have hatched after 1.5 times the development time of an untreated control. 100% means that no flies have hatched; 0% means that all flies have hatched normally.

In this test the compounds of Preparation Examples 1 and 2, for example, showed an activity of 100% at an exemplary active compound concentration of 100 ppm.

Example E

Test with *Boophilus microplus* resistant/SP-resistant Parkhurst strain

Test animals: Adult females which have sucked themselves full

Solvent: Dimethyl sulphoxide 20 mg of active compound are dissolved in 1 ml of dimethyl sulphoxide, while dilute concentrations are prepared by dilution with dist. $H_2O$.

10 adult *Boophilus microplus* res. are dipped for 1 minute into the preparation of active compound to be tested. The animals are transferred into plastic beakers and kept in a climatized room, and the kill rate is then determined.

100% means that all ticks have been killed; 0% means that none of the ticks have been killed.

In this test the compound of Preparation Example 1, for example, showed an activity of 100% at an exemplary active compound concentration of 100 ppm.

Example F

Test with *Boophilus microplus* resistantlSP-resistant Parkhurst strain

Test animals: Adult females which have sucked themselves full

Solvent: Dimethyl sulphoxide 20 mg of active compound are dissolved in 1 ml of dimethyl sulphoxide, while dilute concentrations are prepared by dilution with the same solvent.

The test is carried out in 5 replications. 1 ml of the solutions is injected into the abdomen, the animals are transferred into dishes and kept in a climatized room. After 7 days, the activity control is carried out for inhibition of oviposition. An activity of 100% means that none of the ticks has deposited eggs.

In this test, the compounds of Preparation Examples 1 and 2, for example, showed an activity of 100% at an exemplary active compound concentration of 20 $\mu$g/animal.

Example G

Test with cat fleas/oral administration

Test animals: Adult *Ctenocephalides felis*

Solvent: Dimethyl sulphoxide (DMSO)

To produce a suitable formulation, a suitable active compound solution is prepared from 20 mg of active compound and 1 ml of DMSO. 15, $\mu$l of this formulation are added to 3 ml of citrated cattle blood, and the mixture is stirred.

10 fasting adult fleas (*Ctenocephalides felis*, "Georgi" strain) are placed into a chamber (Ø 3.2 cm) whose top and bottom are closed with gauze. A metal cylinder whose bottom is closed with parafilm is placed on to the chamber. The cylinder contains 3 ml of blood/active compound formulation which can be taken up by the fleas through the parafilm membrane. The blood is warmed to 37° C., while the temperature in the flea chambers is adjusted to 25° C. Controls are mixed with the same volume of DMSO without addition of a compound. The test is carried out in three replications.

After 28 hours, the mortality in % (=dead fleas) is determined.

In this test the compound of Preparation Example 2, for example, showed an activity of 100% at an exemplary active compound concentration of 100 ppm.

Example H

Phaedon larvae test

Solvent: 7 parts by weight of dimethylformamide

Emulsifier: 1 part by weight of alkylaryl polyglycol ether

To produce a suitable preparation of active compound[ 1] part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all caterpillars have been killed; 0% means that none of the caterpillars have been killed.

In this test, the compounds of Preparation Examples 1 to 9, for example, show a kill of 100% after 7 days, at an exemplary active compound concentration of 0.1%.

What is claimed is:
1. A substituted 3-thiocarbamoylpyrazole of the formula (I):

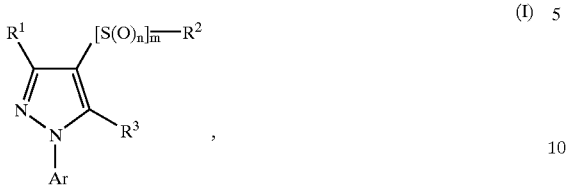

wherein
R¹ represents H₂N—CS—,
m represents the number 0 or 1,
n represents the number 0,1 or 2,
R² represents cyano-($C_1$–$C_4$)-alkyl, thiocyanato-($C_1$–$C_4$)-alkyl, nitro-($C_1$–$C_4$)-alkyl, ($C_1$–$C_6$)-alkylthio-($C_1$–$C_4$)-alkyl, ($C_1$–$C_6$)-alkylsulphinyl-($C_1$–$C_4$)-alkyl, ($C_1$–$C_6$)-alkylsulphonyl-($C_1$–$C_4$)-alkyl, ($C_1$–$C_4$)-halogenoalkylthio-($C_1$–$C_4$)-alkyl having 1 to 6 halogen atoms, ($C_1$–$C_4$)-halogenoalkylsulphinyl-($C_1$–$C_4$)-alkyl having 1 to 6 halogen atoms, ($C_1$–$C_4$)-halogenoalkylsulphonyl-($C_1$–$C_4$)-alkyl having 1 to 6 halogen atoms, ($C_2$–$C_6$)-alkenylthio-($C_1$–$C_4$)-alkyl, ($C_2$–$C_6$)-alkenylsulphinyl-($C_1$–$C_4$)-alkyl, ($C_2$–$C_6$)-alkenylsulphonyl-($C_1$–$C_4$)-alkyl, ($C_2$–$C_6$)-alkynylthio-($C_1$–$C_4$)-alkyl, ($C_2$–$C_6$)-alkynylsulphinyl-($C_1$–$C_4$)-alkyl, ($C_2$–$C_6$)-alkynylsulphonyl-($C_1$–$C_4$)-alkyl, ($C_1$–$C_4$)-alkoxy-carbonyl-($C_1$–$C_4$)-alkyl, ($C_1$–$C_4$)-halogenoalkoxy-carbonyl-($C_1$–$C_4$)-alkyl having 1 to 5 halogen atoms, ($C_1$–$C_6$)-alkoxy-carbonyl, ($C_1$–$C_6$)-alkyl-carbonyl, ($C_1$–$C_6$)-alkoxy-($C_1$–$C_4$)-alkyl, ($C_1$–$C_6$)-halogenoalkoxy-($C_1$–$C_4$)-alkyl having 1 to 6 halogen atoms, ($C_1$–$C_4$)-alkoxy-($C_1$–$C_4$)-alkylthio-($C_1$–$C_4$)-alkyl, ($C_1$–$C_4$)-alkoxy-($C_1$–$C_4$)-alkylsulphinyl-($C_1$–$C_4$)-alkyl, alkoxy-($C_1$–$C_4$)-alkylsulphonyl-($C_1$–$C_4$)-alkyl, ($C_1$–$C_4$)-halogenoalkoxy-($C_1$–$C_4$)-alkylthio-($C_1$–$C_4$)-alkyl having 1 to 5 halogen atoms, ($C_1$–$C_4$)-halogenoalkoxy-($C_1$–$C_4$)-alkylsulphinyl-($C_1$–$C_4$)-alkyl having 1 to 5 halogen atoms, ($C_1$–$C_4$)-halogenoalkoxy-($C_1$–$C_4$)-alkylsulphonyl-($C_1$–$C_4$)-alkyl having 1 to 5 halogen atoms, ($C_1$–$C_4$)-alkylamino-($C_1$–$C_4$)-alkyl, di-($C_1$–$C_4$)-alkylamino-($C_1$–$G_4$)-alkyl, tri-($C_1$–$C_4$)-alkylsilyl-($C_1$–$C_4$)-alkyl; or represents ($C_5$–$C_6$)-cycloalkenyl or ($C_3$–$C_6$)-cycloalkyl-($C_1$–$C_2$)-alkyl, which is optionally mono- to pentasubstituted by substituents selected from the group consisting of ($C_1$–$C_4$)-alkyl, ($C_1$–$C_4$)-alkoxy, halogen, ($C_1$–$C_4$)-halogenoalkyl having 1 to 5 halogen atoms and ($C_1$–$C_4$)-halogenoalkoxy having 1 to 5 halogen atoms; or represents phenyl, phenyl-($C_1$–$C_2$)-alkyl, phenoxy-($C_1$–$C_2$)alkyl, phenylthio-($C_1$–$C_2$)-alkyl, phenylsulphinyl-($C_1$–$C_2$)-alkyl, phenylsulphonyl-($C_1$–$C_2$)-alkyl, phenyl-($C_1$–$C_2$)-alkyloxy-($C_1$–$C_2$)-alkyl, phenyl-($C_1$–$C_2$)-alkylthio-($C_1$–$C_2$)-alkyl, phenyl-($C_1$–$C_2$)-alkylsulphinyl-($C_1$–$C_2$)-alkyl, phenyl-($C_1$–$C_2$)-alkylsulphonyl-($C_1$–$C_2$)-alkyl, the phenyl moiety of which is optionally mono- to trisubstituted by substituents selected from the group consisting of halogen, ($C_1$–$C_6$)-alkyl, ($C_2$–$C_6$)-alkenyl, ($C_1$–$C_6$)-alkoxy, ($C_2$–$C_6$)alkenyloxy, ($C_1$–$C_4$)-alkylthio, ($C_2$–$C_4$)-alkylsulphinyl, ($C_1$–$C_4$)-alkylsulphonyl; ($C_1$–$C_6$)-halogenoalkyl, ($C_2$–$C_4$)-halogenoalkenyl, ($C_1$–$C_4$)-halogenoalkoxy, ($C_{1-4}$)-halogenoalkylthio, ($C_1$–$C_4$)-halogenoalkylsulphinyl and ($C_1$–$C_4$)-halogenoalkylsulphonyl having 1 to 5 halogen atoms; cyano, nitro, hydroxyl, hydrazino, ($C_1$–$C_6$)-dialkylhydrazino, amino, ($C_1$–$C_6$)-alkylamino, di-($C_1$–$C_6$)-alkylamino, ($C_1$–$C_6$)-alkylimino, ($C_1$–$C_4$)-alkyl-carbonyl, ($C_1$–$C_4$)-alkyl-carbonyloxy, phenyl or phenoxy, which is optionally mono- to trisubstituted by substituents selected from the group consisting of halogen, ($C_1$–$C_4$)-alkyl, ($C_1$–$C_4$)-halogenoalkyl having 1 to 5 halogen atoms, ($C_1$–$C_4$)-alkoxy and ($C_1$–$C_4$)-halogenoalkoxy and ($C_1$–$C_4$)-halogenoalkylthio having 1 to 5 Halogen atoms, SF₅ or the grouping

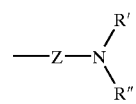

wherein
R' and R" independently represent hydrogen or ($C_1$–$C_6$)-alkyl and
Z represents —CO or —SO₂,
R² where m=0, represents thiocyanato, chlorine, bromine, iodine, nitro, cyano, hydroxyl, chlorosulphonyl, ($C_1$–$C_4$)-alkoxy, ($C_2$–$C_4$)-alkenyloxy; ($C_1$–$C_4$)-halogenoalkyl, ($C_2$–$C_4$)-halogenoalkenyl, ($C_1$–$C_4$)-halogenoalkoxy and ($C_2$–$C_4$)-halogenoalkenyloxy having 1 to 5 halogen atoms; ($C_1$–$C_4$)-alkyl-carbonyloxy, formyl, tri-($C_1$–$C_4$)-alkylsilylethinyl or represents phenoxy which is optionally mono- to pentasubstituted by the phenyl substituents mentioned above for R², or represents one of the following groupings:
—NHR⁴, —NR⁴R⁵, —NHNH₂, —CONH₂, —CSNH₂, —CONR⁴R⁵, —SO₂NR⁴R⁵, —CR⁶=NOR⁷, —CH(OH)R⁸ or —CH(CN)OR⁹,
wherein
R⁴ and R⁵ independently represent hydrogen, cyano, ($C_1$–$C_4$)-alkyl or represent phenyl or benzyl, which is optionally mono- to pentasubstituted by the phenyl substituents mentioned above for R²,
R⁶ represents hydrogen or ($C_1$–$C_4$)-alkyl,
R⁷ represents hydrogen, ($C_1$–$C_4$)-alkyl or benzyl, which is optionally mono- to pentasubstituted by the phenyl substituents mentioned above for R²,
R⁸ represents ($C_1$–$C_4$)-alkyl or ($C_1$–$C_4$)-halogenoalkyl having 1 to 5 halogen atoms,
R⁹ represents ($C_1$–$C_4$)-alkyl,
R³ represents hydrogen, amino, chlorine, bromine, iodine or represents one of the following groupings: —NH—CO—R¹⁰, —NHR¹¹, —OR¹², —SR¹² or —NR¹³—CX—C(R¹⁴, R¹⁵, R¹⁶),
wherein
R¹⁰ represents ($C_1$–$C_4$)-alkyl, ($C_1$–$C_4$)-halogenoalkyl having 1 to 5 halogen atoms, ($C_1$–$C_4$)-alkoxy-($C_1$–$C_4$)-alkyl or represents phenyl or phenoxy, which is optionally mono- to pentasubstituted by the phenyl substituents mentioned above for R²,
R¹¹ represents ($C_1$–$C_4$)-alkyl, ($C_2$–$C_4$)-alkenyl, ($C_2$–$C_4$)-alkynyl, formyl, ($C_1$–$C_4$)-alkyl-carbonyl, ($C_1$–$C_4$)-halogenoalkyl-carbonyl having 1 to 5 halogen atoms or ($C_1$–$C_4$)-alkoxy-carbonyl,
R¹² represents ($C_1$–$C_4$)-alkyl, ($C_2$–$C_4$)-alkenyl, ($C_2$–$C_4$)-alkynyl, di-($C_1$–$C_4$)-alkylamino-($C_1$–$C_4$)-alkyl; phenyl-($C_1$–$C_2$)-alkyl which is optionally mono- to pentasubstituted by the phenyl substituents mentioned above for $R^2$;

or represents the grouping —P(=Y)(OR$^{17}$)(SR$^{18}$), wherein $R^{17}$ and $R^{18}$ independently represent $(C_1-C_4)$-alkyl and Y represents oxygen or sulfur, $R^{13}$ represents hydrogen, $(C_1-C_4)$-alkyl, $(C_1-C_4)$-alkoxy-$(C_1-C_4)$-alkyl, propargyl, allyl, $(C_1-C_4)$-alkoxy-carbonyl, $(C_1-C_4)$-alkyl-carbonyl; or represents benzyl which is optionally mono- to pentasubstituted by the phenyl substituents mentioned above for $R^2$, or represents the grouping —CO—C($R^{14}$, $R^{15}$, $R^{16}$), $R^{14}$ represents hydrogen, $(C_1-C_4)$-alkyl, halogen, $(C_1-C_4)$-halogenoalkyl having 1 to 5 halogen atoms or represents phenyl which is optionally mono- to pentasubstituted by the phenyl substituents mentioned above for $R^2$, $R^{15}$ represents hydrogen, $(C_1-C_4)$-alkyl, halogen, $(C_{1-4})$-halogenoalkyl and $(C_1-C_4)$-halogenoalkoxy-$(C_1-C_4)$-alkyl having 1 to 5 halogen atoms, $(C_1-C_4)$-alkylthio-$(C_1-C_4)$-alkyl, $(C_1-C_4)$-alkylsulphinyl-$(C_1-C_4)$-alkyl, $(C_1-C_4)$-alkylsulphonyl-$(C_1-C_4)$-alkyl, $(C_1-C_4)$-alkoxy-[$(C_1-C_4)$-alkoxy]$_r$-$(C_1-C_4)$-alkyl where r=0 to 2, hydroxyl, $(C_1-C_4)$-alkoxy-carbonyl-$(C_1-C_4)$-alkyl and $(C_1-C_4)$-alkoxy, $R^{16}$ represents hydroxyl, $(C_1-C_4)$-alkoxy, $(C_1-C_4)$-halogenoalkoxy having 1 to 5 halogen atoms or $(C_1-C_4)$-alkoxy-[$(C_1-C_4)$-alkoxy]q wherein q=1 or 2, X represents oxygen or sulfur and Ar represents phenyl which is optionally mono- to trisubstituted by the phenyl substituents mentioned above for $R^2$.

2. The substituted 3-thiocarbamoylpyrazole of claim 1, wherein $R^1$ represents $H_2N$—CS—, m represents the number 0 or 1, n represents the number 0, 1 or 2, $R^2$ represents cyano-$(C_1-C_2)$-alkyl, thiocyanato-$(C_1-C_2)$-alkyl, nitro-$(C_1-C_2)$-alkyl, $(C_1-C_4)$-alkylthio-$(C_1-C_2)$-alkyl, $(C_1-C_4)$-alkylsulphinyl-$(C_1-C_2)$-alkyl, $(C_1-C_4)$-alkylsulphonyl-$(C_1-C_2)$-alkyl, $(C_1-C_2)$-halogenoalkylthio-$(C_1-C_2)$-alkyl having 1 to 5 halogen atoms selected from the group consisting of fluorine, chlorine and bromine, $(C_1-C_2)$-halogenoalkylsulphinyl-$(C_1-C_2)$-alkyl and $(C_1-C_2)$-halogeno-alkylsulphonyl-$(C_1-C_2)$-alkyl having 1 to 5 halogen atoms selected from the group consisting of fluorine, chlorine and bromine, $(C_2-C_4)$-alkenylthio-$(C_1-C_2)$-alkyl, $(C_2-C_4)$-alkynylthio-$(C_1-C_2)$-alkyl, $(C_1-C_2)$-alkoxy-carbonyl-$(C_1-C_2)$-alkyl, $(C_1-C_2)$-halogenoalkoxy-carbonyl-$(C_1-C_2)$-alkyl having 1 to 5 halogen atoms selected from the group consisting of fluorine, chlorine and bromine, $(C_1-C_4)$-alkoxy-carbonyl, $(C_1-C_4)$-alkyl-carbonyl, $(C_1-C_4)$-alkoxy-$(C_1-C_2)$-alkyl, $(C_1-C_2)$-alkoxy-$(C_1-C_2)$-alkylthio-$(C_1-C_2)$-alkyl, $(C_1-C_2)$-halogenoalkoxy-$(C_1-C_2)$-alkylthio-$(C_1-C_2)$-alkyl having 1 to 5 halogen atoms selected from the group consisting of fluorine, chlorine and bromine, $(C_1-C_2)$-alkylamino-$(C_1-C_2)$-alkyl, di-$(C_1-C_2)$-alkylamino-$(C_1-C_2)$-alkyl; or represents phenyl, benzyl, phenoxymethyl, phenoxyethyl, phenylthiomethyl, phenylthioethyl, benzyloxymethyl, benzylthiomethyl, the phenyl moiety of which is optionally mono- to trisubstituted by substituents selected from the group consisting of fluorine, chlorine, bromine, $(C_1-C_4)$-alkyl, allyl, $(C_1-C_4)$-alkoxy, allyloxy, $(C_1-C_2)$-alkylthio; $(C_1-C_2)$-halogenoalkyl or $(C_1-C_2)$-halogenoalkoxy or $(C_1-C_2)$-halogenoalkylthio having 1 to 5 halogen atoms selected from the group consisting of fluorine, chlorine and bromine; cyano, nitro, hydroxyl, hydrazino, dimethylhydrazino, amino, methylamino, dimethylamino, iminomethyl, $(C_1-C_2)$-alkyl-carbonyl, $(C_1-C_2)$-alkyl-carbonyloxy; phenyl or phenoxy, which is optionally mono- to disubstituted by substituent(s) selected from the group consisting of fluorine, chlorine, bromine, methyl, ethyl, methoxy, trifluoromethyl, trifluoromethoxy and trifluoromethylthio; $SF_5$ or the grouping

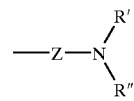

wherein

R' and R" independently represent hydrogen or $(C_1-C_4)$-alkyl and

Z represents —CO or —$SO_2$, $R^2$ where m=0, represents SCN, chlorine, iodine, nitro, cyano, hydroxyl, chlorosulphonyl, $(C_1-C_2)$-alkoxy, allyloxy, $(C_1-C_2)$-halogenoalkyl or $(C_1-C_2)$-halogenoalkoxy having 1 to 5 halogen atoms selected from the group consisting of fluorine, chlorine and bromine; $(C_1-C_2)$-alkyl-carbonyloxy, formyl, —C≡C—Si($CH_3$)$_3$; or represents phenoxy which is optionally mono- to disubstituted by substituents mentioned above for $R^2$; or represents —$CONH_2$, —$CSNH_2$, —CON($CH_3$)$_2$, —CON($C_2H_5$)$_2$, —CH=$NOCH_3$, —CH=$NOC_2H_5$, —C($CH_3$)=$NOCH_3$ and —CH(OH)$CF_3$, $R^3$ represents hydrogen, amino, chlorine, $(C_1-C_4)$-alkylamino and also represents the grouping —NH—CO—$R^{10}$, wherein $R^{10}$ represents $(C_1-C_4)$-alkyl, $(C_1-C_2)$-halogenoalkyl having 1 to 5 halogen atoms selected from the group consisting of fluorine, chlorine and bromine and also represents phenyl and phenoxy, which is optionally mono- to disubstituted by the phenyl substituents mentioned above for $R^2$ and Ar represents phenyl which is optionally mono- to trisubstituted by substituents selected from the group consisting of fluorine, chlorine, bromine; $(C_1-C_2)$-halogenoalkyl and $(C_1-C_2)$-halogenoalkoxy and $(C_1-C_2)$-halogenoalkylthio and $(C_1-C_2)$-halogenoalkylsulphinyl and $(C_1-C_2)$-halogenoalkylsulphonyl having 1 to 5 halogen atoms selected from the group consisting of fluorine, chlorine and bromine; $(C_1-C_2)$-alkyl, $(C_1-C_2)$-alkoxy, hydrazino, dimethylhydrazino, amino, methylamino, dimethylamino, cyano, $SF_5$ or the grouping

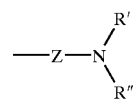

wherein
R' and R" independently represent hydrogen or (C₁–C₄)-alkyl and
Z represents CO or SO₂.

3. The substituted 3-thiocarbamoylpyrazole of claim 1, wherein

R¹ represents H₂N—CS—,
m represents the number 0 or 1,
n represents the number 0, 1 or 2,
R² represents —CH₂—CN, —CH₂-SCN, —CH₂—NO₂, —CH₂—S—CH₃, —CH₂—S—C₂H₅, —CH₂CH₂—S—CH₃, —CH₂CH₂—S—C₂H₅, —CH₂—SO—C₂H₅, —CH₂—SO₂—C₂H₅, —CH₂—S—CF₃, CH₂—SO—CF₃, CH₂—SO₂-CF₃, —CH₂—S—CH₂—CH=CH₂—CH₂—S—CH₂—C≡CH, —CH₂—CO—OCH₃, —CH₂—CO—OC₂H₅, —(CH₂)₂—CO—OCH₃, —(CH₂)₂—CO—OC₂H₅, —CH₂—CO—OCF₃, —CO—OCH₃, —CO—OC₂H₅, —CO—CH₃, —CO—C₂H₅, —CH₂—OCH₃, —CH₂-OC₂H₅, —CH₂—S—CH₂CH₂—O—C₂H₅, —CH₂—S—CH₂CH₂—O—CH₂CF₃, —CH₂—NHC₂H₅, —CH₂CH₂—N(CH₃)₂, —CH₂CH₂—N(C₂H₅)₂, or represents benzyl, benzyloxymethyl, benzylthiomethyl, phenoxymethyl, phenoxyethyl, phenylthiomethyl or phenylthioethyl, which is optionally mono- to trisubstituted by fluorine, chlorine, trifluoromethyl, trifluoromethoxy, trifluoromethylthio, methoxy, hydrazino, dimethylhydrazino, amino, methylamino, dimethylamino, cyano, methylthio, —CONH₂, —CSNH₂, phenyl, chlorophenyl, fluorophenyl, dichlorophenyl, phenoxy, chlorophenoxy, fluorophenoxy and dichlorophenoxy,
R² where m=0, represents SCN, chlorine, iodine, nitro, —OCH₃, —CF₃, —OCF₃, —O—COCH₃,

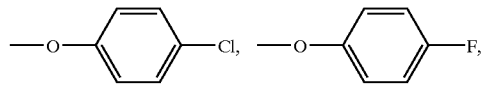

—CSNH₂, —CON(CH₃)₂, —CH=NOCH₃ and —CH(OH)CF₃,
R³ represents hydrogen, amino, chlorine, —NHCH₃, —NHC₂H₅, —NH—CO—CF₃,

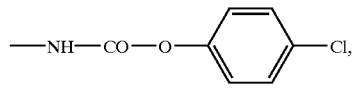

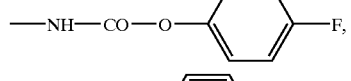

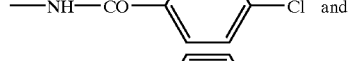

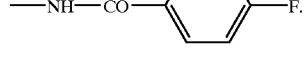

and Ar represents phenyl which is di- or trisubstituted by substituent(s) selected from the group consisting of F, Cl, Br, CF₃, OCF₃, SCF₃, SOCF₃, SO₂CF₃, OCH₂CF₃, CH₃ and SF₅.

4. A 3-Thiocarbamoylpyrazole of the formula (Ia):

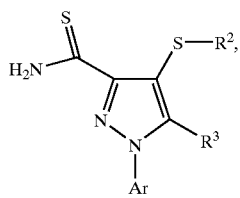

(Ia)

wherein

Ar, R² and R³ are as defined in claim 1.

5. A process for controlling at least one pest selected from the group consisting of insects, arachnids and nematodes comprising applying an effective amount of a compound of claim 1 to said pest and/or its habitat.

6. A pesticide composition comprising one or more 3-thiocarbamoylpyrazoles of claim 1 and one or more materials selected from the group consisting of liquid solvents, solid carriers, surfactants and mixtures thereof.

7. The substituted 3-thiocarbamoylpyrazole of claim 1, wherein

Ar represents

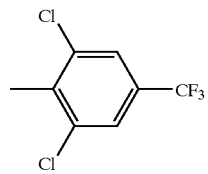

R² represents —S—(CH₂)₂—CO—O—C₂H₅
R³ represents NH₂ and m=1, n=0.

8. A process for preparing the substituted 3-thiocarbamoylpyrazole of claim 7, comprising reacting hydrogen sulphide with a 3-cyanopyrazole of the formula (II):

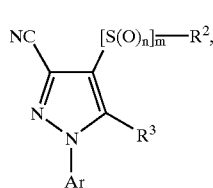

(II)

wherein Ar, R², R³, m and n are as defined in claim 7, and collecting the reaction product.

* * * * *